United States Patent [19]

Sadun et al.

[11] Patent Number: 4,818,091
[45] Date of Patent: Apr. 4, 1989

[54] SYSTEM AND METHOD OF DETECTING VISUAL FIELD DEFECTS

[75] Inventors: Alfredo A. Sadun, San Marino; Michael Wall, New Orleans, both of Calif.

[73] Assignee: University of Southern California, Los Angeles, Calif.

[21] Appl. No.: 815,368

[22] Filed: Dec. 31, 1985

[51] Int. Cl.$^4$ .......................... G02C 7/12; A61B 3/07
[52] U.S. Cl. ..................................... 351/49; 351/224; 351/232
[58] Field of Search ............... 351/237, 239, 240, 241, 351/242, 243, 49, 224, 225, 226, 232, 223, 246

[56] References Cited

U.S. PATENT DOCUMENTS

| | | | |
|---|---|---|---|
| 1,780,291 | 11/1930 | Cameron | 351/237 |
| 1,795,752 | 3/1931 | Bauersfeld et al. | 351/237 |
| 3,074,397 | 1/1963 | Gernet | 351/49 |
| 3,269,792 | 8/1966 | Mirsky | 351/237 |
| 3,415,594 | 12/1968 | Aulhorn | 351/237 |
| 3,416,857 | 12/1968 | Lookabaugh | 351/246 |
| 3,787,112 | 1/1974 | Lyons | 351/223 |
| 3,902,795 | 9/1975 | Owen | 351/224 |
| 4,145,123 | 3/1979 | Krahn et al. | 351/226 |
| 4,511,228 | 4/1985 | Von Glerke et al. | 351/237 |

FOREIGN PATENT DOCUMENTS 465298 9/1928 Fed. Rep. of Germany .
706306 3/1954 United Kingdom .

OTHER PUBLICATIONS

Proceedings of the IEEE, vol. 120, No. 11, Nov. 1973, pp. 1321-1327; G. B. B. Chaplin et al.: "Automated system for testing visual fields" *Abstract paragraph 3.1: "Outline description"*.
Medical Process through Technology, vol. 7, No. 2/3, 1980, pp. 125-128, Springer-Verlag, Berlin, DE; J. R. Charlier: "A new instrument for automatic subjective and objective perimetry" *pp. 125, 126*.
IEEE Transactions on Bio-Medical Engineering, vol. BME-13, No. 1, Jan. 1966, pp. 11-18; G. D. Beinhocker et al.: "Electroperimetry" *Abstract*.

"Amsler Charts", The Optician, vol. CXXII, pp. XVII and 384, Nov. 2, 1951.
PCT International Search Report dated Mar. 20, 1987.
Operation instructions and description manual for automated perimeter system sold under the trademark "Octopus".
Article by Alfredo A. Sadun & Michael Wall entitled "Threshold Amsler Grid Testing: Cross Polarizing Lenses Further Enhance Yield" published in Archives of Ophthalomogy, vol. 104, pp. 520–523 (1986).
Article by Mainster & Dieckert entitled "A Simple Haploscopic Method for Quantitating Color Brightness Comparison" published in American Journal of Ophthalmology, vol. 89, No. 1, pp. 58–61 (1980).
Article entitled "Brightness-Sense and Optic Nerve Disease" published in Archives of Ophthalmology, vol. 103, pp. 39–43 (Jan., 1985).

Primary Examiner—Deborah L. Kyle
Assistant Examiner—Michael J. Carone
Attorney, Agent, or Firm—Pretty, Schroeder, Brueggemann & Clark

[57] ABSTRACT

A method and system are provided for detecting and monitoring the treatment of eye disease by determining the presence of visual field defects. The method utilizes eyeglasses having a pair of cross-polarizing lenses selectively adjustable for varying the amount of luminance of an Amsler grid as observed by the patient through the eyeglasses. By adjusting the relative polarization of the lenses separately for each eye until the patient is barely able to see the Amsler grid, the sensitivity of the patient's eyes to the presence of scotomas is greatly increased. By having patients record the presence of scotomas while observing the Amsler grid through the eyeglasses, it is possible to screen patients for visual loss associated with various eye diseases, such as atrophic SMD. Recording the existence of scotomas on a periodic basis enables an ophthalmologist to determine whether atrophic SMD may be advancing to hemorrhagic SMD requiring treatment to prevent permanent loss of central vision.

18 Claims, 2 Drawing Sheets

SYSTEM AND METHOD OF DETECTING VISUAL FIELD DEFECTS

BACKGROUND OF THE INVENTION

This invention relates to a system and method of detecting and monitoring the treatment of eye disease by determining the presence of visual field defects.

According to recent studies, senile macular degeneration ("SMD") has been determined as one of the leading causes of blindness in the U.S. and Western Europe. The cause of SMD presently is unknown, and the disease may be a result of the aging process. In its mildest form, SMD is a cumulation of changes in the eye which include loss of photoreceptors, accumulation of drusen, pigmentary changes, retinal pigment epithelial cell damage, and other changes. When these changes reach a point in their progression that impairment of central vision occurs, the condition is known as dry or atrophic SMD. This vision impairment typically results in a central visual field defect in the form of a scotoma, i.e., a blind spot. Some scotomas may be detected by kinetic and static tangent screen examination, by threshold automated perimetry and, on occasion, through standard Amsler grid testing.

A small percentage of patients with SMD develop a much more serious form of the disease known as disciform or hemorrhagic SMD. In this advanced form of the disease, new small vessels escape their confinement from the choriod and enter the inner sanctum of the eye under the retina through breaks in Bruch's membrane. In this new subretinal location, the vessels proliferate into a network of vessels that eventually leak protein and bleed, causing localized detachments and irreversible damage to the photoreceptors at the macula. Hemorrhagic SMD is extremely disabling because it severely damages central vision, thus affecting the ability to read and drive. The transition of the disease from the relatively mild atrophic SMD to the more serious hemorrhagic SMD takes place in a relatively short three to four week period. After this three to four week period, hemorrhaging of the subretinal new vessels can occur at any time and produce disastrous permanent damage to central vision.

Known methods of determining this new vessel growth include tangent screen examination and threshold automated perimetry. If the scotomas indicating the presence of atrophic SMD have increased in size from previous tests, then it is an indication that new vessel growth may be occurring. Attempts to use standard Amsler grid testing as another method generally have failed because it is a supra-threshold test lacking sufficient sensitivity to accurately and consistently detect the presence of relative scotomas in the central visual field.

Fortunately, there are treatments for the disease during the critical three to four week period of new vessel growth to prevent advancement to the severe stage of hemorrhagic SMD. One of the more recent effective treatments has been photocoagulation treatment, in which a laser beam is used to destroy and halt the growth of the new vessels under the retina. Once the vessels are destroyed, protein and blood outflow usually stop, and the potential for further vessel growth is minimized.

Unfortunately, however, the existing methods for detecting new vessel growth, prior to advancement of the disease to hemorrhagic SMD, are time consuming, relatively expensive, or unreliable. Thus, while patients who have developed atrophic SMD should be tested frequently to identify the presence or absence of new vessel growth, many are reluctant or financially unable to undergo testing on such a frequent basis. Many patients often are confronted with the dilemma of balancing the needs of their time and finances with the horrible possibility that they may permanently lose their central vision if not tested frequently enough to detect the new vessel growth. Moreover, there is the statistical consideration that only a small percentage of those with atrophic SMD, approximately five to fifteen percent, go on to develop hemorrhagic SMD.

Accordingly, there has existed a definite need for an efficient and reliable system and method of detecting and monitoring atrophic SMD before the disease advances to the severe stage of hemorrhagic SMD. There also generally has existed a need for a system and method of detecting visual field defects that is inexpensive and not time consuming. The present invention satisfies these needs and provides further related advantages.

SUMMARY OF THE INVENTION

The present invention provides a method and system for detecting and monitoring visual field defects and, particularly, central visual field defects indicating the condition known as senile macular degeneration ("SMD"). The method and system further provide for treating atrophic SMD before it advances into hemorrhagic SMD. The method utilizes eyeglasses having a pair of cross-polarizing lenses selectively adjustable for varying the amount of luminance of an Amsler grid as observed by the patient through the eyeglasses. By adjusting the relative polarization of the lenses separately for each eye until the patient is barely able t see the Amsler grid, the sensitivity of the patient's eyes to the presence of scotomas is greatly increased. By having patients record the presence of scotomas while observing the Amsler grid through the eyeglasses, it is possible to screen patients for visual loss associated with atrophic SMD. By subsequently recording the existence of scotomas on a periodic basis, it can be determined whether the condition may be advancing to hemorrhagic SMD, which can be treated by known methods, such as photocoagulation treatment. The method and system of this invention furthermore are intended to be inexpensive and simple to implement, and relatively accurate and reliable in result.

The eyeglasses used in practicing the method of this invention comprise a frame having two oculars in visual alignment with a patient's eyes. A pair of supports extending from the oculars wrap around the patient's ears and position the eyeglasses securely in front of the patient's eyes. A substantially transparent, polarized inner lens fixed against rotation is mounted in each ocular. Another substantially transparent, polarized outer lens is rotatably mounted in front of each fixed inner lens. Rotation of the outer lenses with respect to the fixed inner lenses over a ninety degree angle of rotation controls the amount of light permitted to collectively pass through the lenses into each eye. The eyeglasses are described and claimed in an application for patent by Alfredo A. Sadun entitled "Method and System for Detecting, Characterizing and Monitoring Optic Nerve Disease", Ser. No. 815,216, filed Dec. 31, 1985.

The method of this invention utilizes a standard Amsler grid and the eyeglasses described above, and comprises the steps of positioning the eyeglasses in front of the patient's eyes and providing the Amsler grid for viewing. Then separately for each eye, one at a time, an ophthalmologist rotates the adjacent outer lens with respect to the inner lens to decrease luminance until the patient can no longer see the Amsler grid. The adjacent outer lens is then rotated with respect to the inner lens in small increments to increase luminance until the patient is barely able to see the Amsler grid. After this, the patient records the existence of any scotomas observed through the one eye viewing the Amsler grid.

By decreasing luminance of the Amsler grid in the manner described above, the ability of the patient to perceive scotomas in the central visual field is enhanced dramatically. This is because the stimulus is barely supra-threshold. Since visual contrast is a function of the difference in luminance between a target and its background decreasing the luminance of the Amsler grid to the level at which the grid can barely be seen enables testing at only slightly above threshold stimulus and, thus, provides an increase in the patient's sensitivity and ability to detect scotomas. Accordingly, this allows the ophthalmologist to quickly and inexpensively detect central visual field defects of numerous visual disorders that might not be detected by standard methods. The detected scotoma alerts the ophthalmologist to the possible presence of atrophic or hemorrhagic SMD.

An important aspect of the method of this invention is in the monitoring of diseases such as atrophic SMD prior to its advancement into hemorrhagic SMD, which occurs in approximately 5-15% of those with atrophic SMD. If the SMD is advancing into the hemorrhagic form, then the size and number of scotomas observed by the patient will increase during a relatively short period of three to four weeks. In proceeding to this advanced form of SMD, new small blood vessels under the retina grow and proliferate until they leak protein and bleed, and the latter usually causes irreversible damage and complete loss of central vision. By periodically testing a patient with atrophic SMD using the method of this invention, the existence of scotoma size and number can be detected in sufficient time to destroy these new vessels before they hemorrhage causing disastrous damage. The vessels can be destroyed using known photocoagulation techniques.

A significant advantage of the method of this invention is that it is highly sensitive and accurately determines the existence of scotomas where other methods indicate no scotomas or define the borders of scotomas more loosely. Moreover, the method is intended to be conveniently carried out in the home by the patient himself without need for costly and time consuming office visits. This is because the eyeglasses are intended to be inexpensive to manufacture and therefore affordable to those with atrophic SMD and other diseases. Use at home will permit more frequent testing, greatly increasing the likelihood of arresting the progression of new vessel growth in time.

Another aspect of the present invention includes a system for detecting and monitoring visual field defects indicating atrophic SMD, permitting treatment of new vessels before atrophic SMD advances into hemorrhagic SMD. The system of detecting and monitoring comprises the Amsler grid, the eyeglasses described above, and means for recording the existence of scotomas separately for each eye when viewing the Amsler grid at a barely supra-threshold stimulus through the eyeglasses. For dealing with atrophic SMD before it advances into hemorrhagic SMD, the system entails well-established laser treatment of the subretinal new blood vessels to prevent hemorrhage thereof and loss of central vision.

Other features and advantages of the present invention will become apparent from the following detailed description, taken in conjunction with the accompanying drawings, which illustrate, by way of example, the principles of the invention.

BRIEF DESCRIPTION OF THE DRAWINGS

The accompanying drawings illustrate the equipment used in the method and system of the invention. In such drawings.

DETAILED DESCRIPTION OF THE PREFERRED EMBODIMENT

Figure 1:
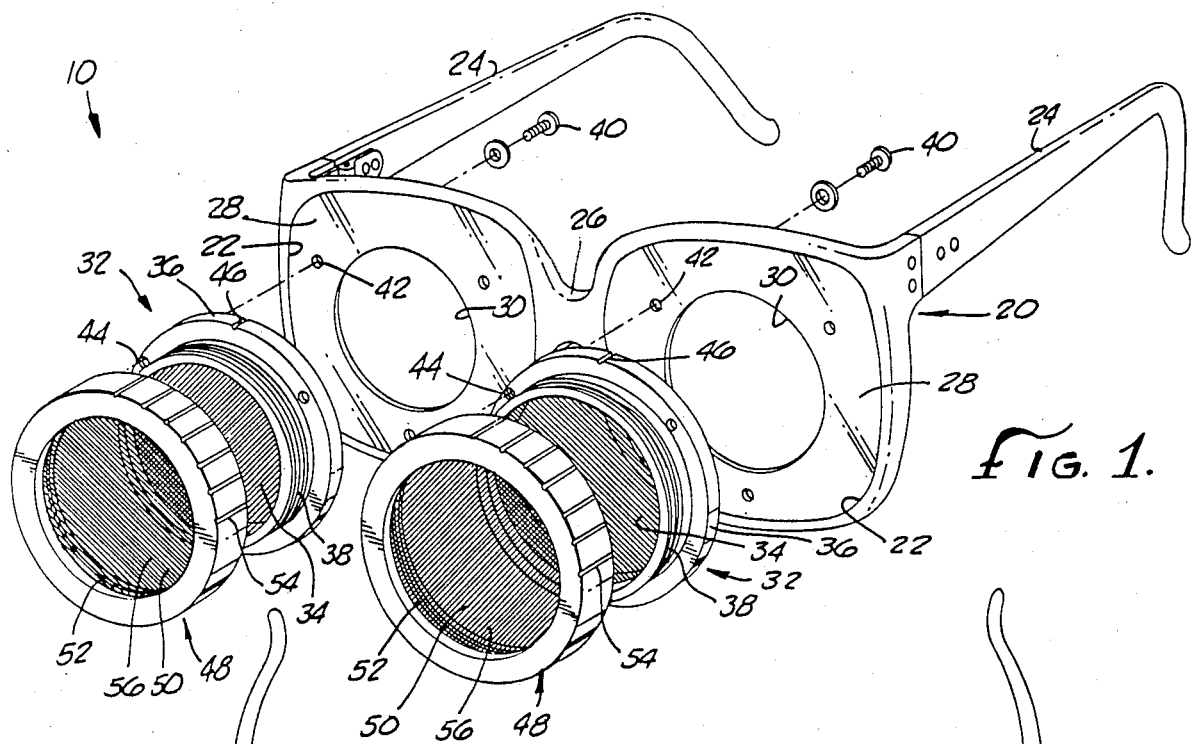
FIG. 1 is an exploded view of the eyeglasses having cross-polarizing lenses shown in an orthogonal relationship to prevent the transmission of light through the lenses.
Figure 2:
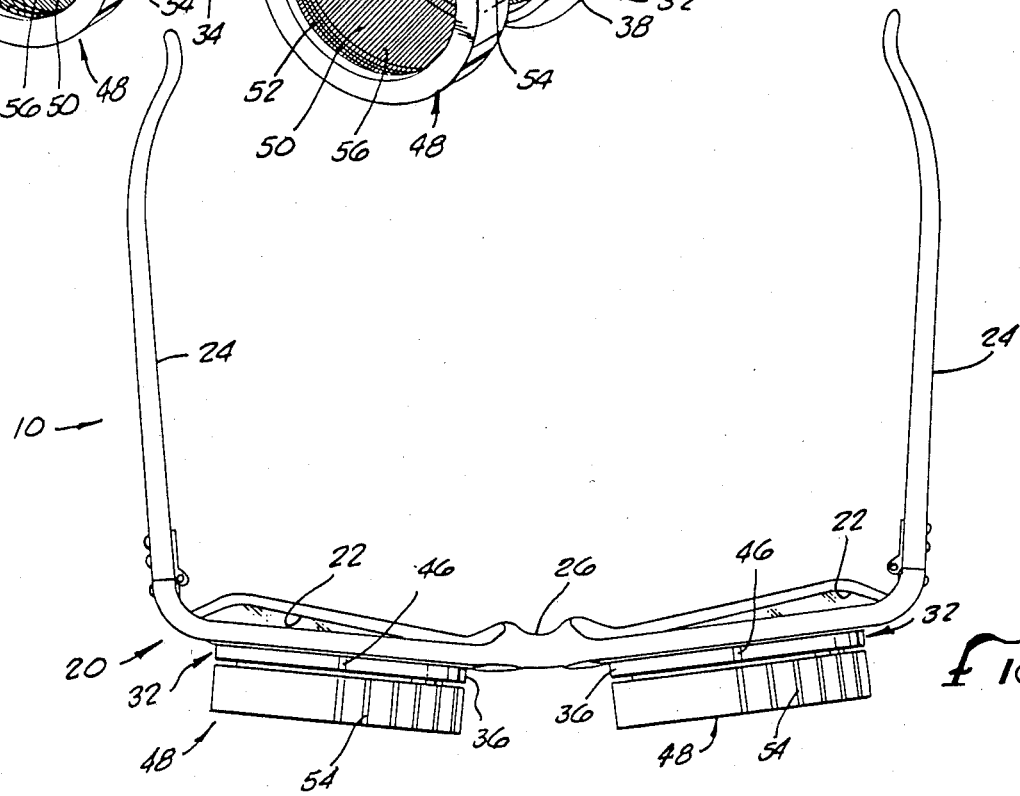
FIG. 2 is a plan view of the eyeglasses of FIG. 1.
Figure 3:
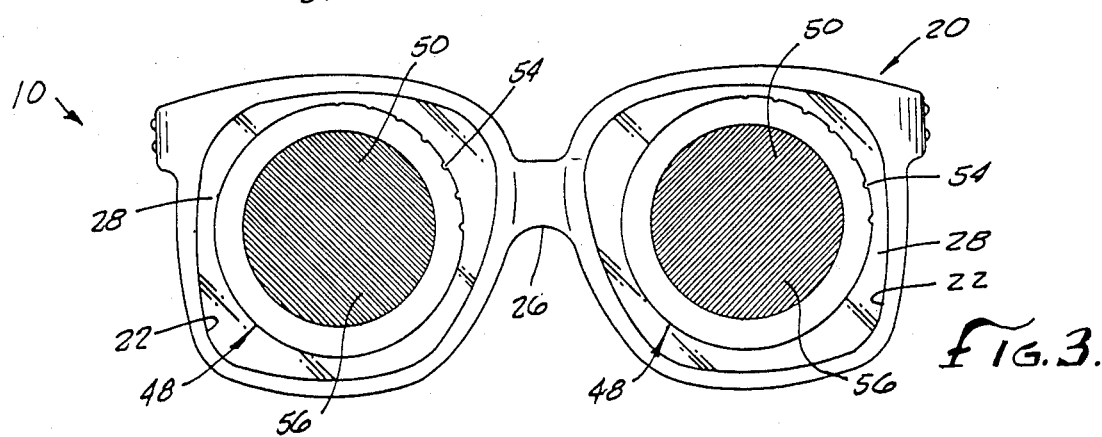
FIG. 3 is a front elevational view of the eyeglasses.

The present invention is embodied in a method and system for detecting and monitoring visual field defects and, particularly, central visual field defects indicating senile macular degeneration ("SMD"). The method and system further provide for detecting, monitoring and treating atrophic SMD before it advances into hemorrhagic SMD. The method utilizes a pair of eyeglasses, generally referred to by the reference numeral 10, for use in creating low luminance conditions for a patient viewing a standard Amsler grid 12 through the eyeglasses. The decreased luminance conditions created by the eyeglasses produce a barely supra-threshold stimulus for the patient and substantially increase the sensitivity of the patient to the presence of scotomas in the central visual field of the affected eye. The presence of relative scotomas in the central visual field helps in the diagnosis of atrophic SMD, and changes in these scotomas suggest that the condition is advancing to hemorrhagic SMD requiring corrective treatment to prevent total loss of central vision. The method of this invention furthermore can be quickly and inexpensively carried out.

Figure 4:
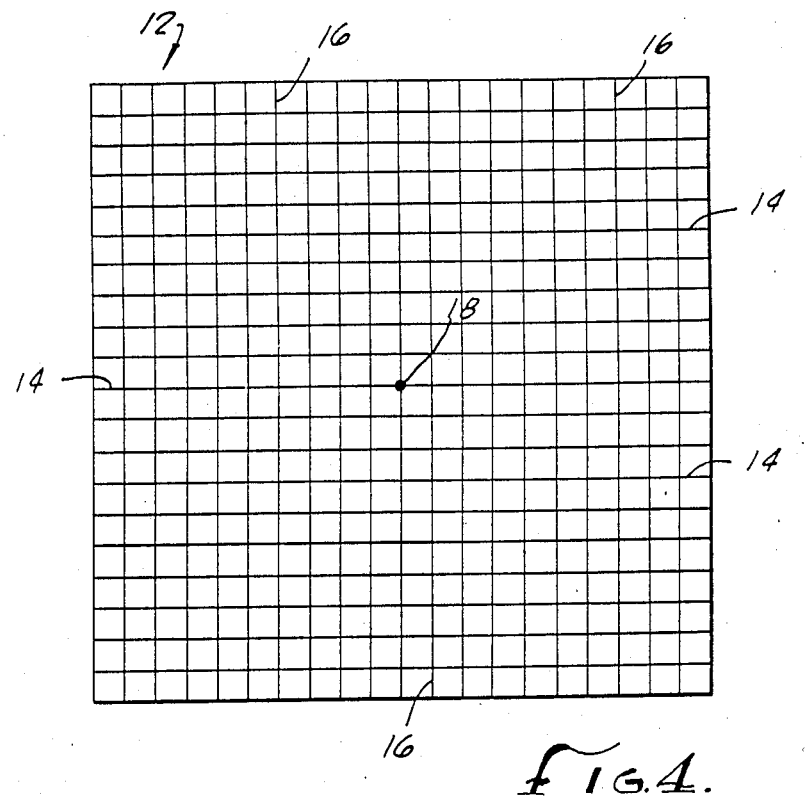
FIG. 4 is an illustration of a standard Amsler grid on a white background.

The equipment used to practice the method of this invention includes the eyeglasses 10 and the standard Amsler grid 12, preferably on a white background as illustrated in FIG. 4, for viewing through the eyeglasses by the patient to be tested for scotomas in the central visual field. The standard Amsler grid comprises a plurality of evenly spaced horizontal and vertical lines 14 and 16 overlapping to form a checkered-type grid on a white background, such as a sheet of white paper. The center of the Amsler grid is indicated by an enlarged dot 18 at the intersection of the center most horizontal and vertical lines. The Amsler grid first was introduced in 1947 and is a commonly used test object for evaluation of the ten degrees of visual field surrounding fixation at the dot. The Amsler grid provides a test object that has a substantially consistent or regular pattern on a substantially homogeneous background and, therefore, is the object most often used by ophthalmologists to evaluate the central visual field for dense or absolute defects. Accordingly, while the method of this invention preferably uses a standard Amsler grid on a white background, it will be appreciated that other test targets that have a substantially consistent or regular pattern on a substantially homogeneous background may be used for evaluating the central visual field.

The eyeglasses 10 comprise a frame 20 including a pair of oculars 22 with elongated supports 24 extending away from the oculars for resting on the patient's ears. A bridge 26 separates the oculars and rests on the patient's nose. The bridge and two supports function together to position and retain the eyeglasses on the patient, with the oculars arranged in visual alignment with the patient's eyes. Within each ocular is a mounting plate 28 having a substantially circular opening 30 in its center to permit unobstructed vision through the oculars. The mounting plate is substantially transparent and snap-fits within the oculars, as would a normal eyeglass lens.

An inner lens mount 32 carrying a substantially transparent polarized inner lens 34 is mounted to the anterior or front surface of each of the plates 28. The inner lens mount is substantially cylindrical and has a radially outwardly extending flange 36 at the rear part of the mount, and an externally threaded outer surface 38 at the front part of the mount. The inner lens mount is secured to the plate by screws 40 extending through holes 42 and 44 in the plate and internally threaded holes in the flange. One of the screws 40, for exemplification, is shown for each lens and it will be understood that the other screws are also present. The screws also prevent rotation of the inner lens mount with respect to the plate and eyeglasses 10. A reference notch 46 also is provided in the outer surface of the flange.

An outer lens mount 48 carrying a substantially transparent polarized outer lens 50 is rotatably mounted to each of the inner lens mounts 32. The outer lens mount is substantially cylindrical and has an internally threaded surface 52 at the rear part of the mount, with the polarized outer lens secured within the front part of the mount. The internal threads of the outer lens mount are adapted to mate with the external threads 38 of the inner lens mount so that the inner and outer lens mounts are threadedly attached to each other. To install the mounts, the outer lens mount preferably is threaded onto the inner lens mount until the threads bottom out, and then the outer lens mount is backed off about a quarter to three quarters of a turn. This permits the outer lens 50 to rotate with respect to the inner lens 34 a sufficient rotational amount for enabling practice of the present invention as described below. The external surface of the outer lens mount contains a plurality of measuring notches 54 which, in the preferred embodiment, are spaced apart at least every fifteen degrees over a ninety degree segment of the external surface of the outer lens mount. That is, there are a minimum of seven measuring notches corresponding to locations on the outer lens mount of 0, 15, 30, 45, 60, 75 and 90 degrees rotation. The reference notch 46 preferably is positioned at the twelve o'clock position on the inner lens mount, as best shown in FIG. 1, to permit easy viewing with respect to the measuring notches 54.

The polarized inner and outer lenses 34 and 50 each have polarizing gratings, as illustrated by the parallel lines 56, which cooperate to selectively control the amount of light permitted to collecting pas through the inner and outer lenses. Thus, when the polarizing gratings of the inner and outer lenses are parallel to each other, the maximum amount of light is permitted to collectively pass through the lenses. When the polarizing gratings are orthogonal, however, the minimum amount of light is permitted to collectively pass through. To determine the relative position of the polarizing gratings of the outer lens with those of the inner lens, the reference notch 46 on the inner lens mount 32 and the measuring notches 54 on the outer lens mount 48 can be positioned accordingly. For example, when the first measuring notch representing zero degrees rotation aligns with the reference notch, the polarizing gratings will be in parallel to permit maximum light transmission. Similarly, when the seventh measuring notch representing ninety degrees rotation aligns with the reference notch, the polarizing gratings are orthogonal for minimum light transmission. For purposes of illustration, FIG. 1 shows the polarizing gratings in an orthogonal relationship, with the seventh measuring notch aligned with the reference notch.

The eyeglasses 10 described above, including the frame 20, inner lens mounts 32 and outer lens mounts 48, can be constructed from rigid plastic or other suitable lightweight materials. The inner and outer lenses 34 and 50 are constructed from a substantially transparent polarized material. If desired, the measuring notches 54 can be increased in number to provide a more refined measurement of relative rotation between the outer and inner lens mounts. In practicing the method of this invention, it has been found that measuring notches spaced apart about every five degrees and provides an optimal degree of accuracy. The eyeglasses are intended to be inexpensive to manufacture and occasionally used at home by the patient, as directed by the ophthalmologist, to monitor the progression of atrophic SMD before it advances to hemorrhagic SMD during the critical 3-4 week period of new vessel growth.

The method of detecting central visual field defects and thus the existence of atrophic SMD is as follows. The eyeglasses 10 are positioned on the patient with the outer lenses 50 preferably at zero degrees rotation with respect to the inner lenses 34 to permit maximum luminance to the eyes. The patient then is requested to observe the Amsler grid 12 through the eyeglasses. Then separately for each eye, one at a time, the ophthalmologist rotates the adjacent outer lens of the eyeglasses away from zero degrees rotation with respect to the inner lens to decrease luminance until the patient can no longer see the Amsler grid in that eye. The other eye may be occluded, or other outer lens for that eye may be rotated to ninety degrees rotation with respect to the inner lens to block out light to that eye. Next, the ophthalmologist rotates the adjacent outer lens of the eyeglasses in the one eye to be tested toward zero degrees rotation with respect to the inner lens in increments of approximately one degree at a time to increase luminance until the patient is barely able to see the Amsler grid. At this point, the stimulus to the tested eye is barely supra-threshold and provides maximum sensitivity of the eye to the existence of scotomas. The patient then is requested to record the presence of any scotomas observed through the one eye viewing the Amsler grid. In practice, the patient may record the scotomas directly on the Amsler grid he or she is viewing by marking the Amsler grid with a marking object, such as a pencil, to outline the scotoma in the location where he perceives it on the grid and blacken it out directly on the grid. By having the patient record the presence of scotomas while observing the Amsler grid 12 through the eyeglasses, it can be determined whether the patient has developed visual loss such as that found in SMD, and whether it has advanced to the atrophic or hemorrhagic stage.

Figure 5:
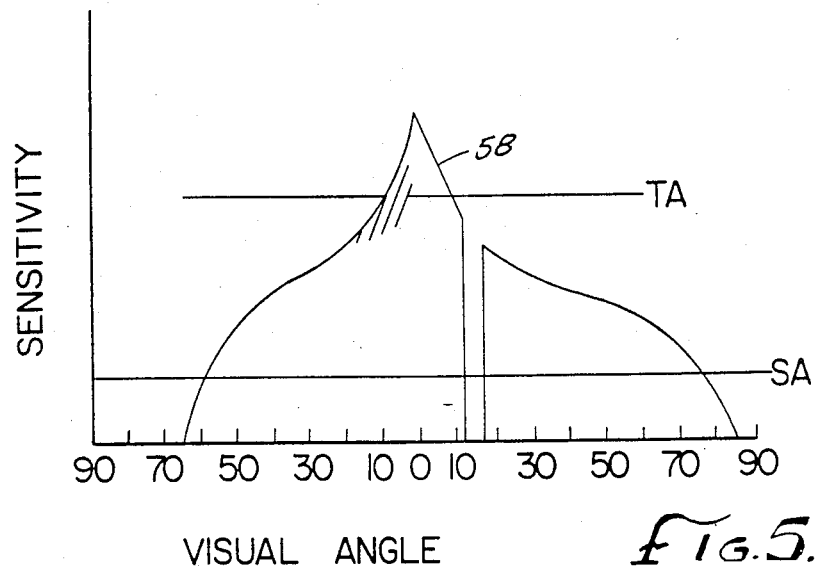
FIG. 5 is a chart illustrating the static profile of the visual field.

Decreasing the luminance of the Amsler grid 12 in the manner described above greatly increases the patient's ability to perceive scotomas in the central visual field. FIG. 5 illustrates a static profile of the visual field for one eye, as indicated by the reference numeral 58. The line identified as TA represents the high degree of sensitivity of the patient to scotomas when viewing the Amsler grid under low luminance conditions created by the eyeglasses. That is, scotomas depressing the visual field below the line TA are perceived by the patient, while scotomas above the line are not. If the patient viewed the standard Amsler grid without the eyeglasses adjusted to provide low luminance conditions, the highest approximate degree of sensitivity obtained is represented by the line marked SA (FIG. 5) in the central visual field. Thus, only scotomas that have depressed the visual field below the line SA are detected, while scotomas above the line have not. Unfortunately, by the time the scotomas have reached a degree of severity to depress the visual field below the SA sensitivity line, the atrophic SMD probably will have advanced to the more severe hemorrhagic SMD, and the central visual field will have been irretrievably lost. As a result, it is not uncommon for there to be scotomas present in the central ten degrees of vision, even when Amsler grid testing under standard conditions otherwise appears normal. This is because relative visual field defects may not be detected with a supra-threshold stimulus, which is the case when viewing a standard Amsler grid under normal room lighting conditions. Because contrast is a function of the difference in luminance between the target an its background, decreasing the luminance of the Amsler grid to the level at which the grid can barely be seen enables testing of the central visual field surrounding fixation at only slightly above threshold. The eyeglasses described above having cross-polarizing lenses conveniently decrease the luminance of the Amsler grid to create a barely supra-threshold stimulus for the highest possible sensitivity to the presence of scotomas.

An important aspect of the method of this invention is the monitoring of atrophic SMD prior to its advancement into hemorrhagic SMD, which occurs in approximately 5-15% of those with atrophic SMD. If the atrophic SMD is advancing into the hemorrhagic form, then the size and number of scotomas observed by the patient will increase during a relatively short period of three to four weeks. During this period, new small blood vessels under the retina grow and proliferate until they leak protein and bleed, which usually causes irreversible damage and complete loss of central vision. By periodically testing a patient with atrophic SMD using the method for detecting visual field defects described above, the existence of scotoma size and number can be monitored over a period of time to detect visual loss from these new sub-retinal vessels and allow for their treatment before they hemorrhage causing disastrous and irreversible damage.

Another aspect of this invention involves the treating of atrophic SMD during the three to four week period in which it advances into hemorrhagic SMD. The method includes the steps of detecting the existence of atrophic SMD and monitoring its progression, as described above, leading to the treatment of the sub-retinal blood vessels during the three to four week period before they hemorrhage. The treatment comprises applying a laser beam to the new blood vessels to destroy them and halt their growth under the retina. Once the vessels are destroyed in this manner, protein and blood outflow usually cease and the potential for further vessel growth is minimized. This type of laser treatment is known as photocoagulation, typically using an argon or krypton laser.

A significant advantage of the method of this invention is its high sensitivity and ability to accurately determine the existence of scotomas. This is accomplished by decreasing the luminance of the Amsler grid 12 to a barely supra-threshold stimulus, as described above. Another significant advantage of the invention is that the eyeglasses are intended to be inexpensive to manufacture and therefore affordable to substantially all persons afflicted with atrophic SMD. By providing the eyeglasses 10 and an Amsler grid 12 to a patient with atrophic SMD, the patient can conveniently and inexpensively monitor the existence of scotomas in the home and determine whether they are increasing in size or number. Thus, the high cost and time consuming nature of separate office visits with the ophthalmologist to undergo current elaborate testing methods, such as kinetic and static tangent screen examination and threshold automated perimetry, is totally avoided. The eyeglasses and standard Amsler grid are intended to be purchased at a comparatively low cost and with the advice of the ophthalmologist, the patient can carry out proper testing and monitoring in the home.

Another aspect of the present invention includes a system for detecting and monitoring central visual field defects indicating atrophic SMD, for treatment of the disease before it advances into the severe hemorrhagic form. The system of detecting and monitoring atrophic SMD comprises the Amsler grid 12 and the eyeglasses 10 described above, and means for recording the existence of scotomas separately for each eye when viewing the Amsler grid at a barely supra-threshold stimulus through the eyeglasses. In the preferred embodiment, the means for recording the existence of scotomas is a hand-held marking instrument, such as a pencil, used by the patient to record directly on the Amsler grid the location of scotomas. For treating atrophic SMD during the three to four week period in which it advances into hemorrhagic SMD, the system further comprises laser treatment of the new sub-retinal blood vessels to prevent their hemorrhage and halt their growth under the retina. In the preferred embodiment, the means for destroying the new sub-retinal blood vessels is a photocoagulation device, such as a laser. After the vessels are destroyed by the laser beam, protein and blood outflow from the vessels normally stop, and the potential for further vessel growth is minimized or eliminated.

From the foregoing, it will be appreciated that the method of this invention can be quickly and inexpensively carried out to detect and monitor visual field defects indicating atrophic SMD, and then to treat that disease prior to its advancement to hemorrhagic SMD. By creating a low luminance, barely supra-threshold stimulus for the patient when viewing the Amsler grid 12, the patient's sensitivity to the existence of scotomas is greatly enhanced and provides highly accurate detection and monitoring of visual field defects. The course of atrophic SMD can be monitored in the home by the patient using the method of this invention, and when it is determined that scotomas are growing in size and number during the three to four week period when the disease advances to the hemorrhagic form, the patient can be examined and treated by the ophthalmologist to prevent potential loss of central vision. The invention further provides a system for detecting and monitoring atrophic SMD in accordance with the method described.

While a particular form of the invention has been illustrated and described, it will be apparent that various modifications can be made without departing from the spirit and scope of the invention. Accordingly, it is not intended that the invention be limited, except as by the appended claims.

We claim:

1. A method of detecting visual field defects in a patient, comprising the steps of:
   (a) providing an illuminated object having a substantially consistent or regular pattern on a substantially homogeneous background for viewing by the patient;
   (b) then separately for each eye, one at a time, fixing the luminance of the object as perceived by the patient so that the object is barely visible by the patient, and having the patient record the presence of any visual field defects observed through the one eye viewing the object.

2. The method of claim 1, wherein the object is an Amsler grid on a white background.

3. A method of detecting visual field defects in a patient, using eyeglasses of the type having a frame with a polarized inner lens fixedly mounted against rotation over at least one ocular of the frame, and a polarized outer lens in visual alignment with and mounted for rotation with respect to the inner lens, the inner lens and outer lenses having their polarized gratings in parallel for maximum light transmission when the outer lens is at zero degrees rotation with respect to the inner lens, and the polarizing gratings being orthogonal for minimum light transmission when the outer lens is at ninety degrees rotation with respect to the inner lens, said method comprising the steps of:
   (a) positioning the eyeglasses over the patient's eyes;
   (b) providing an Amsler grid for viewing through the eyeglasses by the patient; and
   (c) then separately for each eye, one at a time, rotating the outer lens of the eyeglasses away from zero degrees rotation with respect to the inner lens to decrease luminance until the patient can no longer see the Amsler grid; rotating the outer lens of the eyeglasses toward zero degrees rotation with respect to the inner lens in small increments to increase luminance until the patient is barely able to see the Amsler grid; and having the patient record the presence of any scotomas observed through the one eye viewing the Amsler grid.

4. The method of claim 3, wherein the outer lens is rotated toward zero degrees rotation with respect to the inner lens in increments of approximately one degree at a time to increase luminance until the patient is barely able to see the Amsler grid.

5. The method of claim 3, wherein the patient records the presence of any visual field defects directly on the Amsler grid with a hand held marking instrument.

6. A system for detecting visual field defects in a patient, comprising:
   (a) an illuminated object having a substantially consistent or regular pattern on a substantially homogeneous background for viewing by the patient;
   (b) means interposed between the patient and the object for fixing the luminance of said object as perceived by the patient so that the object is barely visible by the patient; and
   (c) means used by the patient for recording the existence of visual field defects observed by the patient separately in each eye when viewing said object.

7. The system of claim 6, wherein said object is an Amsler grid on a white background.

8. The system of claim 6, wherein said means for varying the luminance of said object is a pair of eyeglasses for positioning in front of the patient's eyes, said eyeglasses including,
   a frame,
   a pair of inner lenses mounted against rotation on said frame in visual alignement with the patient's eyes, said pair of inner lenses being constructed from a substantially transparent, polarized material, and
   a pair of outer lenses in visual alignment with and mounted for rotation with respect to said pair of inner lenses, said pair of outer lenses being constructed from a substantially transparent, polarized material, rotation of said pair of outer lenses with respect to said pair of inner lenses over a ninety degree angle varying the amount of light allowed to collectively pass through said pair of inner and outer lenses, selective independent rotation of said pair of outer lenses with respect to the inner lenses causing the luminance of said object as perceived by the patient to be increased or diminished.

9. The system of claim 6, wherein said means for recording the existence of visual field defects comprises a pencil used by the patient to identify areas directly on the Amsler grid corresponding to a visual field defect.

10. A system for detecting visual field defects in a patient, comprising:
   (a) an illuminated object having a substantially consistent or regular pattern on a substantially homogeneous background for viewing by the patient;
   (b) eyeglasses for mounting in front of the patient's eyes, said eyeglasses having;
   a frame;
   a pair of inner lenses mounted on said frame in visual alignment with the patient's eyes, said pair of inner lenses being constructed from a substantially transparent, polarized material, and
   a pair of outer lenses mounted on said frame in visual alignment with said pair of inner lenses, said pair of outer lenses being constructed from a substantially transparent, polarized material, relative rotation between said pair of inner and outer lenses with respect to each other over a ninety degree angle varying the amount of light allowed to collectively pass through said pair of inner and outer lenses, selective independent rotation of one of said lenses with respect to the other of said lenses causing the luminance of said object perceived by the patient to be increased or diminished; and
   (c) means used by the patient for recording the existence of visual field defects observed by the patient separately in each eye when viewing said illuminated object through said eyeglasses with one of the lenses of said eyeglasses rotated with respect to the other lens such that said illuminated object is barely visible.

11. The system of claim 10, wherein said illuminated object is an Amsler grid on a white background.

12. The system of claim 11, wherein said means for recording the existence of visual field defects includes a marking object used by the patient to identify areas on the Amsler grid corresponding to a visual field defect.

13. The system of claim 12, wherein the marking object is a hand held marking instrument.

14. A method of monitoring atrophic senile macular degeneration by determining an increase in the number or size of visual field defects in a patient, using eyeglasses of the type having a frame with a pair of polarized inner lenses mounted against rotation in each ocular of the frame and a pair of polarized outer lenses in visual alignment with and mounted for rotation with respect to the inner lenses, the inner and outer lenses having their polarizing gratings in parallel for maximum light transmission when the outer lenses are at zero degrees rotation with respect to the inner lenses, and the polarizing gratings being orthogonal for minimum light transmission when the outer lenses are at ninety degrees rotation with respect to the inner lenses, said method comprising the steps of:
    (a) positioning the eyeglasses in front of the patient's eyes;
    (b) providing an Amsler grid for viewing through the eyeglasses by the patient;
    (c) then separately for each eye, one at a time,
    rotating the adjacent outer lens of the eyeglasses away from zero degrees rotation with respect to the inner lens to decrease luminance until the patient can no longer see the Amsler grid,
    rotating the adjacent outer lens of the eyeglasses toward zero degrees rotation with respect to the inner lens in increments of approximately one degree at a time to increase luminance until the patient is barely able to see the Amsler grid,
    having the patient record the presence of any visual field defects observed through the one eye viewing the Amsler grid, and
    (d) repeating steps (a)–(c) periodically until the presence of previously observed visual field defects decreases, thereby indicating resolution of new blood vessel growth in senile macular degeneration, or until the presence of previously observed visual field defects increases during a period of approximately two to four weeks, thereby indicating progression of the atrophic macular degeneration to hemorrhagic senile macular degeneration through new blood vessel growth.

15. A method of detecting visual loss for determining intervention for treatment of atrophic senile macular degeneration before the condition develops into hemorrhagic senile macular degeneration in which sub-retinal blood vessels proliferate until they hemorrhage, using eyeglasses of the type having a frame with a pair of polarized inner lenses mounted against rotation in each ocular of the frame and a pair of polarized outer lenses in visual alignment with and rotatably mounted for rotation with respect to the inner lenses, the inner and outer lenses having their polarizing gratings in parallel for maximum light transmission when the outer lenses are at zero degrees rotation with respect to the inner lenses, and the polarized gratings being orthogonal for minimum light transmission when the outer lenses are at ninety degrees rotation with respect to the inner lenses, said method comprising the steps of:
    (a) positioning the eyeglasses in front of the patient's eyes;
    (b) providing an Amsler grid for viewing through the eyeglasses by the patient;
    (c) then separately for each eye, one at a time,
    rotating the adjacent outer lens of the eyeglasses away from zero degrees rotation with respect to the inner lens to decrease luminance until the patient can no longer see the Amsler grid,
    rotating the adjacent outer lens of the eyeglasses toward zero degrees rotation with respect to the inner lens in increments of approximately one degree at a time to increase luminance until the patient is barely able to see the Amsler grid, and
    having the patient record the presence of any visual field defects observed through the one eye viewing the Amsler grid; and
    (d) repeating steps (a)–(c) periodically until a noticable increase in the number or size of scotomas has occurred during a period of approximately two to four weeks.

16. The method of claim 1, wherein the object is an Amsler grid.

17. The system of claim 6, wherein said object is an Amsler grid.

18. The system of claim 10, wherein said object is an Amsler grid.

* * * * *